United States Patent
Watkinson et al.

(10) Patent No.: US 9,616,117 B2
(45) Date of Patent: Apr. 11, 2017

(54) ANTHRAX VACCINE FORMULATION AND USES THEREOF

(75) Inventors: Allan Watkinson, Guisborough (GB); David Woodhouse, Yarm (GB); Robert Wilson, Cumbernauld (GB)

(73) Assignee: PharmAthene, Inc., Annapolis, MD (US)

( * ) Notice: Subject to any disclaimer, the term of this patent is extended or adjusted under 35 U.S.C. 154(b) by 584 days.

(21) Appl. No.: 12/998,245

(22) PCT Filed: Oct. 2, 2009

(86) PCT No.: PCT/GB2009/051293
§ 371 (c)(1),
(2), (4) Date: Jun. 15, 2011

(87) PCT Pub. No.: WO2010/038076
PCT Pub. Date: Apr. 8, 2010

(65) Prior Publication Data
US 2011/0236425 A1 Sep. 29, 2011

Related U.S. Application Data

(60) Provisional application No. 61/194,967, filed on Oct. 2, 2008.

(51) Int. Cl.
*A61K 39/07* (2006.01)
*A61K 39/39* (2006.01)
*A61K 39/00* (2006.01)

(52) U.S. Cl.
CPC ............. *A61K 39/07* (2013.01); *A61K 39/39* (2013.01); *A61K 2039/545* (2013.01); *A61K 2039/55505* (2013.01); *A61K 2039/60* (2013.01)

(58) Field of Classification Search
None
See application file for complete search history.

(56) References Cited

U.S. PATENT DOCUMENTS

| | | | |
|---|---|---|---|
| 4,127,385 | A | 11/1978 | Weeke |
| 4,486,530 | A | 12/1984 | David et al. |
| 4,891,319 | A | 1/1990 | Roser et al. |
| 6,267,958 | B1 | 7/2001 | Andya et al. |
| 7,329,513 | B2 | 2/2008 | Bhatnagar et al. |
| 7,348,006 | B2 * | 3/2008 | Contorni et al. .......... 424/184.1 |
| 7,537,771 | B2 | 5/2009 | Williamson et al. |
| 8,277,816 | B2 | 10/2012 | Yusibov et al. |
| 2003/0170263 | A1 | 9/2003 | Williamson et al. |
| 2005/0112145 | A1 | 5/2005 | Hudson et al. |
| 2005/0266021 | A1 | 12/2005 | Maa et al. |
| 2007/0154494 | A1 | 7/2007 | Mikszta et al. |
| 2008/0226729 | A1 | 9/2008 | Sullivan et al. |
| 2011/0142870 | A1 | 6/2011 | Yusibov et al. |

FOREIGN PATENT DOCUMENTS

| | | |
|---|---|---|
| EP | 0745388 | 12/1996 |
| EP | 1972347 | 9/2008 |
| GB | 1561042 | 2/1980 |
| WO | WO 98/08952 | 3/1998 |
| WO | WO 01/93829 | 12/2001 |
| WO | WO 02/04646 | 1/2002 |
| WO | WO 02/100340 | 12/2002 |
| WO | WO 03/040179 | 5/2003 |
| WO | WO 03/048390 | 6/2003 |
| WO | WO 2004/073735 | 9/2004 |
| WO | WO 2005/123131 | 12/2005 |
| WO | WO 2005/123764 | 12/2005 |
| WO | WO 2006/037070 | 4/2006 |
| WO | WO 2007/068902 | 6/2007 |
| WO | WO 2007/122373 | 11/2007 |
| WO | WO 2008/079464 | 7/2008 |
| WO | WO 2008/152654 | 12/2008 |
| WO | WO 2009/093072 | 7/2009 |
| WO | WO 2010/038076 | 4/2010 |
| WO | WO 2010/084298 | 7/2010 |

OTHER PUBLICATIONS

Williamson et al (Infection and Immunity, 73(9):5978-5987, 2005).*
Puziss et al (Journal of Bacteriology, 85(1):230-236, 1963).*
Berthold et al, Vaccine 23:1993-1999, 2005.*
Bedu-Addo, Pharmacological Technology, Lyophilization, 2004, pp. 10-18.
Chauhan et al., BBRC, vol. 283, pp. 308-315 (2001).
Crowe et al., Biophysical J., vol. 71, pp. 2087-2093 (1996).
Crowe et al., Ann. Rev. Physiol., vol. 60, pp. 73-103 (1998).
Duddu & Dal Monte, Pharmaceutical Research, vol. 14, p. 591-595 (1997).
Gribbon et al., Dev. Biol. Stand., vol. 87, pp. 193-199 (1996).
Gupta et al., Protein Expression and Purification, vol. 16, pp. 369-376 (1999).
Houen & Koch, J. Immunological Methods, vol. 200, pp. 99-105 (1997).
Ivins et al., Vaccine, vol. 13, pp. 1779-1784 (1995).
Iyer et al., Pharmaceutical Dev. and Technology, vol. 8, pp. 81-86 (2003).
Izutsu et al., Pharmaceutical Res., vol. 11, p. 995-999 (1994).
Jendrek et al. Vaccine, vol. 21, pp. 3011-3018 (2003).
Jiang et al., J. Pharm. Sci., vol. 95, pp. 80-96 (2006).
Katz et al., J. Virological Methods, vol. 12, pp. 193-198 (1985).
Katz et al., J. Virological Methods, vol. 25, pp. 101-108 (1989).
Lindblad, E. B., "Mineral Adjuvants" in *Immunopotentiators in Modern Vaccines*, Eds. Schijns and O'Hagan, Academic Press (2006), pp. 217-233.
Mikszta et al., J. Infectious Diseases, vol. 191, pp. 278-288 (2005).

(Continued)

*Primary Examiner* — Patricia Duffy
(74) *Attorney, Agent, or Firm* — Raymond J. Lillie; Alan J. Grant

(57) ABSTRACT

An anthrax vaccine with alhydrogel as the adjuvant is presented in a composition formulated by mixing rPA with colloidal alhydrogel (alum) adjuvant to produce the final product, comprising 200 µg/ml rPA bound to 0.26% alhydrogel in phosphate buffered saline (PBS), said formulation containing an optimal concentration of phosphate. Methods of using the vaccines to treat or prevent infections are also presented.

15 Claims, 10 Drawing Sheets

(56) References Cited

OTHER PUBLICATIONS

Mohammed et al., "Lyophylization and Sterilization of liposomal vaccines to produce stable and sterile products" in Methods: A Companion to Methods in Enzymology, Academic Press, NY, vol. 40, No. 1, pp. 30-38 (2006).
Rinella et al., Vaccine, vol. 14, pp. 298-300 (1996).
Rinella et al., J. Colloid Interface Sci., vol. 172, pp. 121-130 (1995).
Rinella et al., Pharmaceutical Research, vol. 10, p. S170 (1993) (Abstract).
Thraenhart, J. Biological Standardization, vol. 17, pp. 291-309 (1989).
Zhu et al., J. Immunol. Methods, vol. 344, pp. 73-78 (2009).
International Search Report for Application PCT/GB2007/001353.
International Search Report for Application PCT/GB2009/050050.
International Search Report for Application PCT/GB2009/050051.
International Search Report for Application PCT/GB2009/051293.
Heine et al., Antimicrob. Agents Chemother., vol. 51, pp. 1373-1379 (2007).
Watkinson et al., Clinical and Vaccine Immunology, vol. 20, pp. 1659-1668 (2013).

* cited by examiner

Figure 6

Mean residue ellipticity [θ] values of rPA DP at 208 nm and 222 nm

| Phosphate concentration (mM) | $[\theta]_{208nm}$ (deg cm² dmol⁻¹) | $[\theta]_{222nm}$ (deg cm² dmol⁻¹) |
|---|---|---|
| 0.25 | -8592 ±96 | -6386 ±206 |
| 2 | -8367 ±250 | -6638 ±121 |
| 3 | -8769 ±716 | -6804 ±293 |
| 4 | -8281 ±588 | -6526 ±349 |
| 5 | -8821 ±116 | -6862 ±120 |
| 7 | -8855 ±69 | -6667 ±33 |
| 10 | -9148 ±517 | -6755 ±160 |

Figure 8

$T_m$ and $\Delta H$ for phosphate effect

| Sample | $T_m$ (°C) | $\Delta H$ (kcal mol$^{-1}$) |
|---|---|---|
| 0.25 | none | none |
| 3 | 43.1 | 51 |
| 4 | 43.8 | 79 |
| 5 | 44.9 | 120 |
| 10 | 46.7 | 165 |
| 50 | 47.7 | 210 |

ANTHRAX VACCINE FORMULATION AND USES THEREOF

This application is a National Phase of International Application PCT/GB2009/051293, filed 2 Oct. 2009, which claims priority of U.S. Provisional Application 61/194,967, filed 2 Oct. 2008, the disclosure of which is hereby incorporated by reference in its entirety.

GOVERNMENT RIGHTS NOTICE

The present invention was produced under government contract N01-AI-30052 with the U.S. National Institutes of Allergy and Infectious Diseases (NIAID), which was subsequently transferred to U.S. Biomedical Advanced Research and Development Authority (BARDA) (and renumbered HSSO100200900103C) so that the U.S. Government may have rights in any patent that issues.

FIELD OF THE INVENTION

The present invention relates to the field of vaccine formulations, such as that containing anthrax protective antigen, and uses of such vaccine, whereby efficacy of such vaccine is both maintained and enhanced.

BACKGROUND OF THE INVENTION

Vaccines are commonly formulated using an adjuvant. A common adjuvant-type is the aluminum based colloids, usually referred to as alum. More specifically these are usually aluminum hydroxide (aluminum oxyhydroxide) (also called alhydrogel) and aluminum phosphate (also called adju-phos). For example, vaccines useful against organisms such as anthrax (*Bacillus anthracis*) are commonly formulated with alhydrogel, which binds the anthrax antigen used in such vaccines (so called subunit vaccines). One aim of such product formulations was to maximize the binding of rPA to the alum. Since phosphate ions were known to desorb antigen from the alhydrogel colloid, the phosphate concentration in such formulations has been kept deliberately low (at 0.25 mM). At this concentration the phosphate buffer does not interfere with rPA binding to the alhydrogel colloid. For example, with this formulation we have found that recombinant protective antigen (rPA) binding was >98%.

Batches of this drug product formulation have been used in the Phase I and Phase II clinical studies, which demonstrated safety and immunogenicity in man.

With this original formulation the pH was found to be 5.9 due to the insufficient buffering capacity of the low phosphate buffer. In order to increase the stability of the rPA drug product and provide a more physiological pH, it was decided that increased control of the formulation was required. The pH of the drug product formulation had to be increased to pH 7 so that an improvement in the buffering capacity of the formulation would be required. For control at pH 7.0, a possible physiological buffer is phosphate, which has a pKa at 7.2 but the disadvantage of using phosphate in the formulation was the inhibitory effect upon rPA-alum binding.

Based on pKa, the possible alternative would be histidine (pKa 6.04), however when stored as a liquid, it has the propensity to oxidize and produce a brown coloration. Moreover, introduction of an alternative buffer such as histidine would mean a radical change in the formulation. A new approach was therefore needed.

We subsequently discovered that we could increase phosphate concentration to a level that both controlled pH and afforded minimal effect on rPA:alhydrogel binding. Consequently, the phosphate concentration was increased to approximately 4 mM; a concentration that was capable of maintaining the Drug Product at a pH of approximately 7.0, and did not markedly affect the amount of unbound rPA, which remained below the level of detection of the assay (<2%).

This led to the surprising result that such a phosphate concentration also greatly increases the bioactivity of the vaccine formulation.

BRIEF SUMMARY OF THE INVENTION

In one aspect, the present invention relates to an anthrax vaccine composition, comprising a therapeutically effective amount of an anthrax antigen in a pharmaceutically acceptable carrier and containing a phosphate salt at a concentration in the range of 2 mM to 10 mM, preferably 2.5 mM to 7.5 mM, more preferably 3 mM to 5 mM, or in the range of 3.5 mM to 4.5 mM, even more preferably in the range of 3.8 mM to 4.2 mM, or in the range of 3.9 mM to 4.1 mM and most preferably is about 4.0 mM.

In specific embodiments, the vaccine comprises an anthrax antigen, preferably an anthrax subunit such as protective antigen, most preferably recombinant protective antigen (rPA). In other embodiments, the vaccine further comprises an adjuvant, preferably alum (alhydrogel). In one embodiment, the vaccine composition is in the form of a lyophilized powder. In another embodiment, the vaccine composition may also comprise phosphate buffered saline (PBS).

In other examples of the vaccine composition or formulation of the invention, the pH of the vaccine composition is in the range of 7.0 to 7.2, preferably about 7.1.

In other examples, the anthrax vaccine formulation of the invention contains alhydrogel (alum) at about 0.15 to 0.35%, preferably at about 0.20 to 0.30%, more preferably at about 0.24 to 0.28%, and most preferably wherein the alhydrogel (alum) is present at about 0.26%.

In a preferred embodiment, the vaccine of the invention is a sub-unit vaccine. In a further embodiment, such sub-unit vaccine is an anthrax vaccine of comprising rPA is present at about 200 µg/ml, wherein phosphate is present at about 4 mM, wherein alhydrogel is present at about 0.26% by weight and wherein the pH of said vaccine is about 7.1.

The present invention further relates to a method of protecting against a bacterial infection in a mammal, comprising administering to a mammal at risk of such infection a therapeutically-effective amount of the vaccine composition of the invention. In further embodiments thereof, the bacterial infection is an anthrax (*Bacillus anthracis*) infection and/or the mammal is a human being.

The present invention also relates to a method of treating a bacterial infection in a mammal, comprising administering to a mammal afflicted with such infection a therapeutically-effective amount of the vaccine composition of the invention. In further embodiments thereof, the bacterial infection is an anthrax (*Bacillus anthracis*) infection and/or the mammal is a human being.

BRIEF DESCRIPTION OF THE DRAWINGS

FIG. 6 shows the effect of phosphate on secondary structure of rPA in a formulated drug product.

FIG. 7 shows the effect of phosphate on tertiary structure of rPA in formulated Drug Product.

FIG. 8 shows the effect of phosphate on rPA melting as determined by DSC.

FIG. 9 shows the effect of phosphate on rPA melting as determined by thermal denaturation/intrinsic fluorescence.

FIG. 10 shows epitope recognition of Drug Product formulated at different phosphate concentrations.

DETAILED DESCRIPTION OF THE INVENTION

The present invention provides an anthrax subunit vaccine formulation containing comprising a therapeutically effective amount of an anthrax antigen, such as anthrax protective antigen (rPA) in a pharmaceutically acceptable carrier and containing a phosphate salt at a concentration of between 2 and 10 mM, preferably between 3 and 5 mM, more preferably about 4 mM, using alhydrogel as adjuvant. The present invention also provides methods for treating or preventing bacterial infections, especially infections of anthrax in a human being, by administering a therapeutically effective amount of a vaccine of the invention.

As used herein the term "effective amount" or "therapeutically effective amount" means a dosage sufficient to treat, inhibit, or alleviate one or more symptoms of a bacterial infection, especially anthrax infection. The precise dosage may vary with such factors as the age, immune system status, general health, and environmental circumstances of the patient, the nature and extent of the infection (or anticipated infection) and the availability of subsequent treatment/vaccination.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutically acceptable carriers, diluents and excipients are generally added that are compatible with the active ingredients and acceptable for pharmaceutical use.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N.J. current edition).

Vaccine compositions may further incorporate additional substances to stabilize pH, or to function as adjuvants, wetting agents, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art, or for administration through nasal or respiratory routes.

The amount of vaccine sufficient to confer immunity to pathogenic bacteria, viruses, or other microbes is determined by methods well known to those skilled in the art in view of the guidance provided herein. This quantity will be determined based upon the characteristics of the vaccine recipient and the level of immunity required (as already noted above). Where vaccines are administered by subcutaneous or intramuscular injection, a range of 0.5 to 500 μg purified protein may be given. As useful in the present invention, such dosages are commonly sufficient to provide about 1 μg, possibly 10 μg, even 50 μg, and as much as 100 μg, up to 500 μg of immunogenic protein, or immunogenic polypeptide, or immunogenically active fragments thereof. In addition, more than one such active material may be present in the vaccine. Thus, more than one antigenic structure may be used in formulating the vaccine, or vaccine composition to use in the methods disclosed herein. This may include two or more individually immunogenic proteins or polypeptides, proteins or polypeptides showing immunogenic activity only when in combination, either quantitatively equal in their respective concentrations or formulated to be present in some ratio, either definite or indefinite.

A vaccine composition for use in the processes disclosed herein may include one or more immunogenic proteins, one or more immunogenic polypeptides, and/or one or more immunogenically active immunogens comprising antigenic fragments of said immunogenic proteins and polypeptides, the latter fragments being present in any proportions selected by the use of the present invention. The exact components, and their respective quantities, making up the vaccines, and vaccine compositions, useful in the methods of the present invention are determined, inter alia, by the nature of the disease to be treated or prevented, the severity of such condition where it already exists, the age, sex, and general health of the recipient, as well the personal and professional experience and inclinations of the researcher and/or clinician utilizing these methods.

For a vaccine of the present invention, such as a sub-unit vaccine for use against anthrax, specific non-limiting examples of this vaccine composition are those wherein said rPA is present at about 10 to 300 μg/ml, preferably 50 to 300 μg/ml, or wherein said rPA is present at about 100 to 300 μg/ml, more preferably about 150 to 250 μg/ml, and most preferably wherein said rPA is present at about 200 μg/ml.

In other examples, the dose of antigen, preferably rPA, to be administered is at least about 5 μg, or at least about 10 μg, or at least about 25 μg, or at least about 50 μg, or at least about 75 μg, or at least about 100 μg, or at least about 150 μg, or at least about 200 μg, with a preferred dose of about 100 μg. A preferred dose volume is about 0.5 ml.

The present invention further relates to a vaccine comprising a purified antigen, preferably an anthrax antigen, more preferably anthrax protective antigen (PA) and most preferably a recombinant anthrax protective antigen (rPA), such as that described in FIG. 2 of WO 2007/122373, pub. 1 Nov. 2007, the disclosure of which is hereby incorporated by reference in its entirety, or that described in WO02/04646, bound to an adjuvant, preferably an alum-based adjuvant. In a preferred embodiment, the present invention relates to a sub-unit vaccine comprising alum-bound rPA, at least about 2 mM and most preferably about 4 mM phosphate salt and at about pH 7.1.

Figure 1:
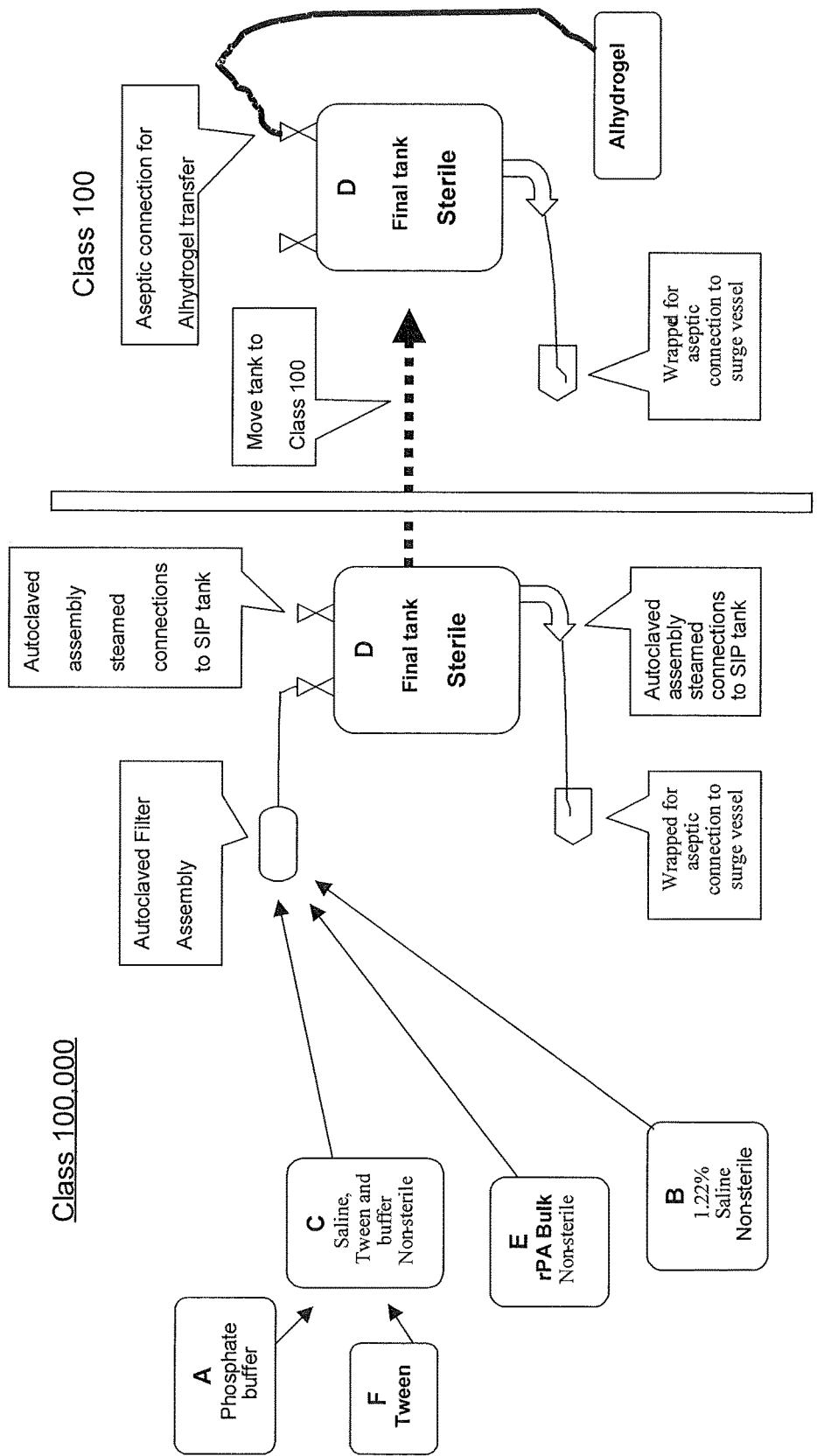
FIG. 1 shows a flowchart for manufacture of a recombinant Protective Antigen (rPA) drug product.
Figure 2:
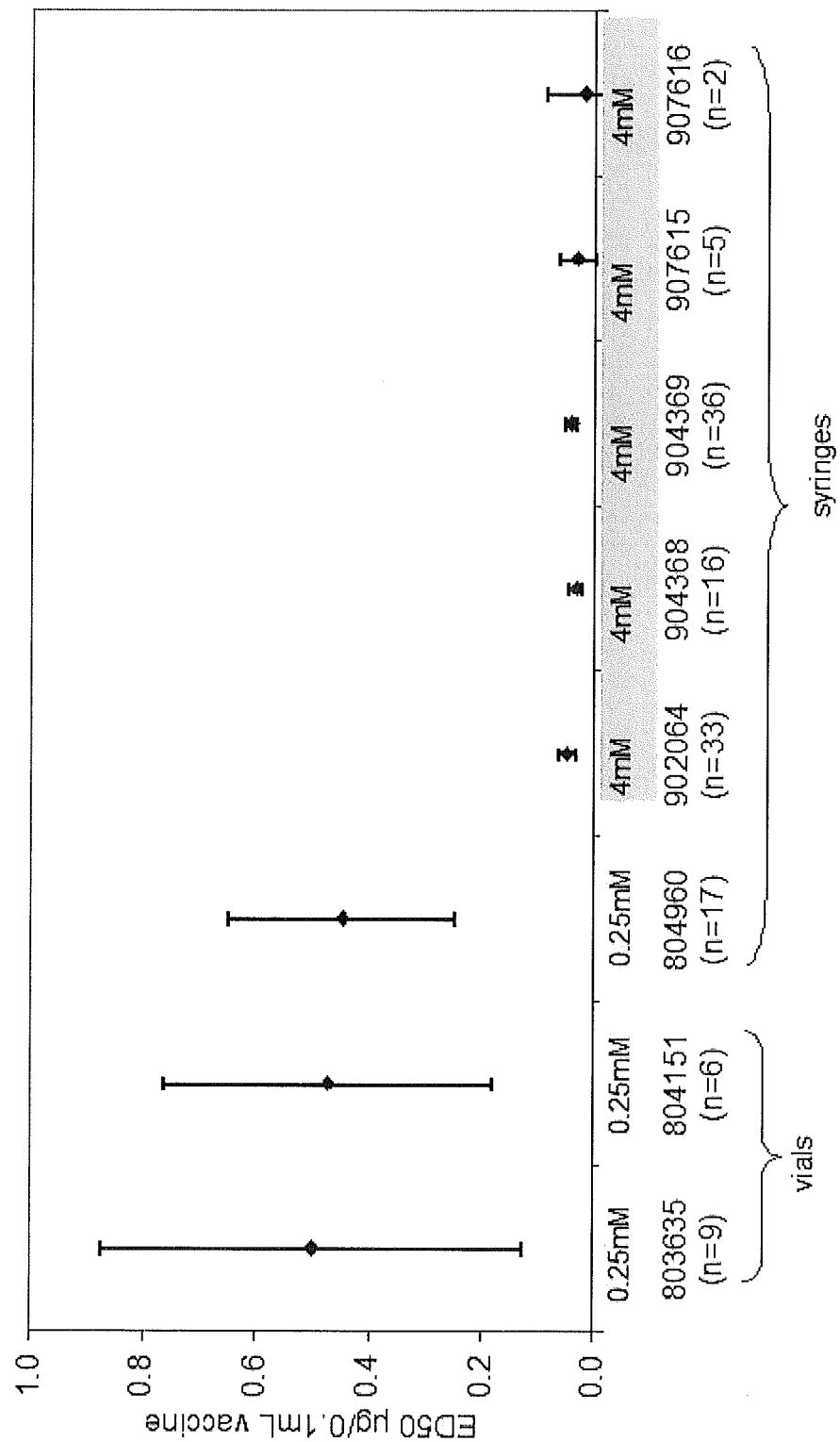
FIG. 2 shows the results of an ED50 comparison of high and low phosphate drug products.
Figure 3:
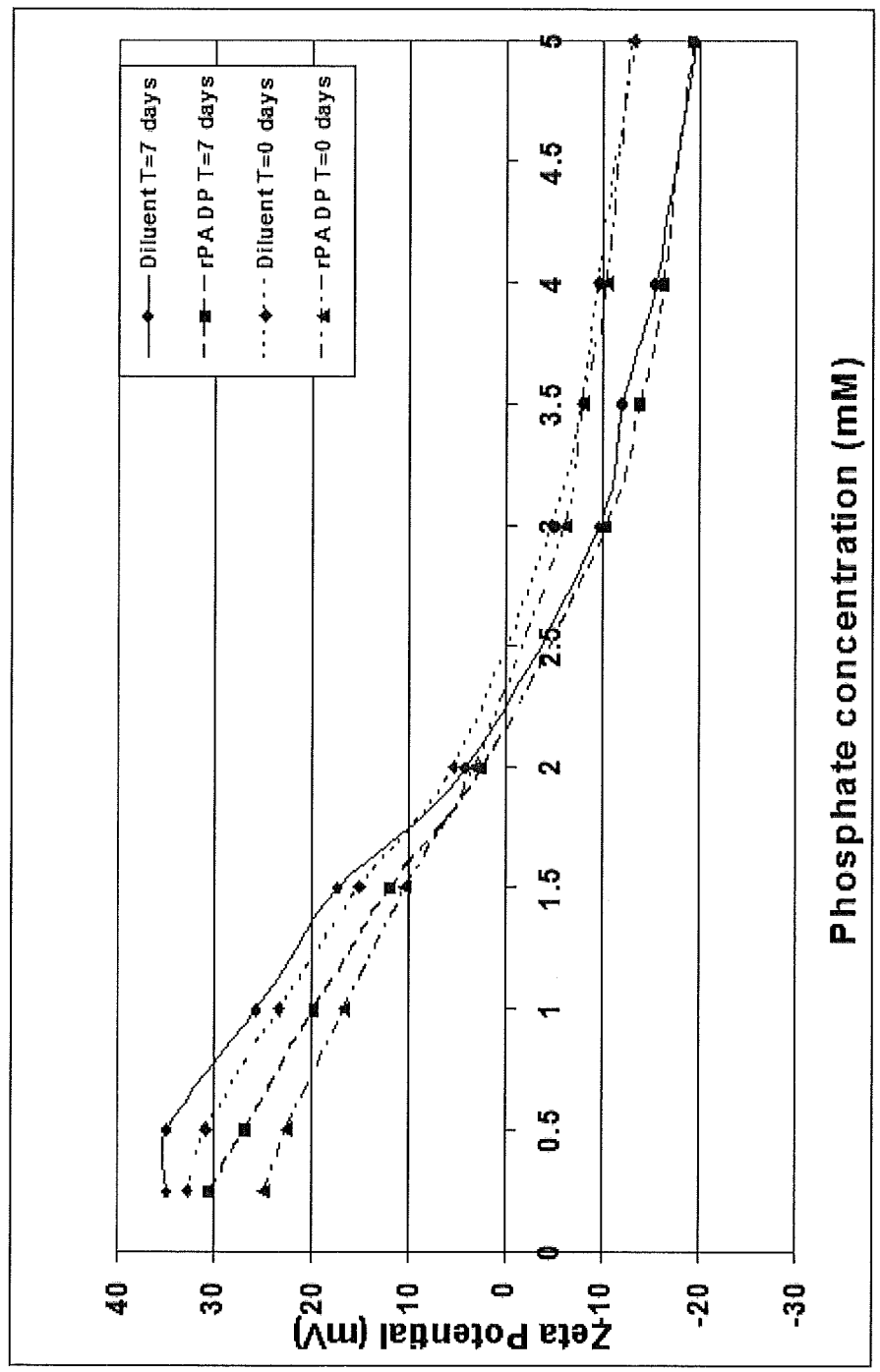
FIG. 3 shows the effect of phosphate on the zeta potential of alhydrogel diluent and drug product.
Figure 4:
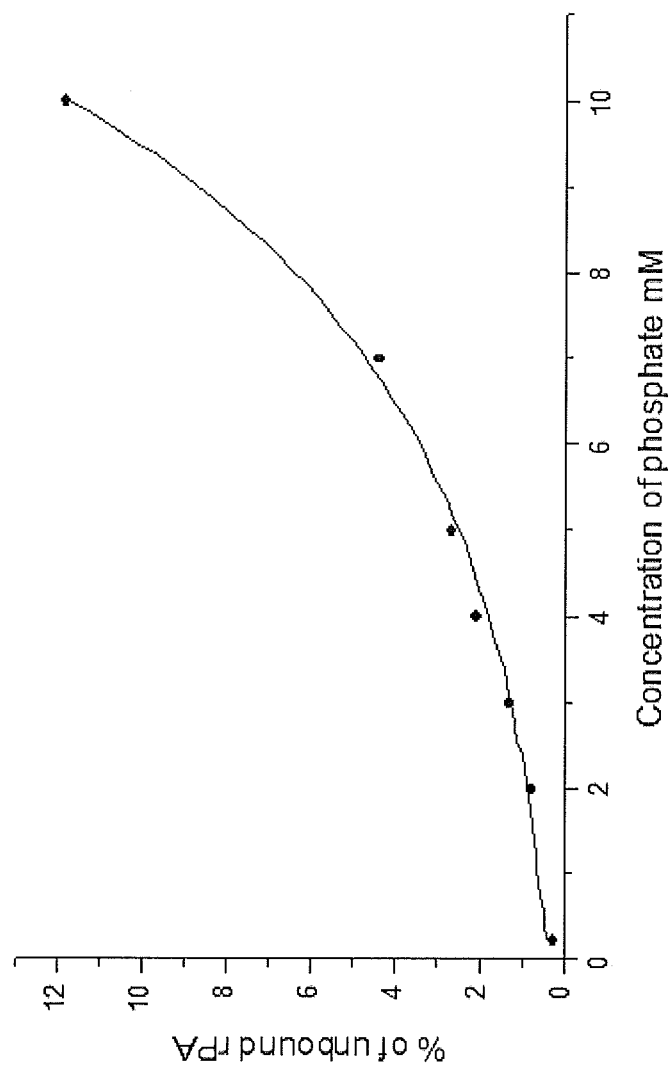
FIG. 4 shows the effects of phosphate on unbound rPA.
Figure 5:
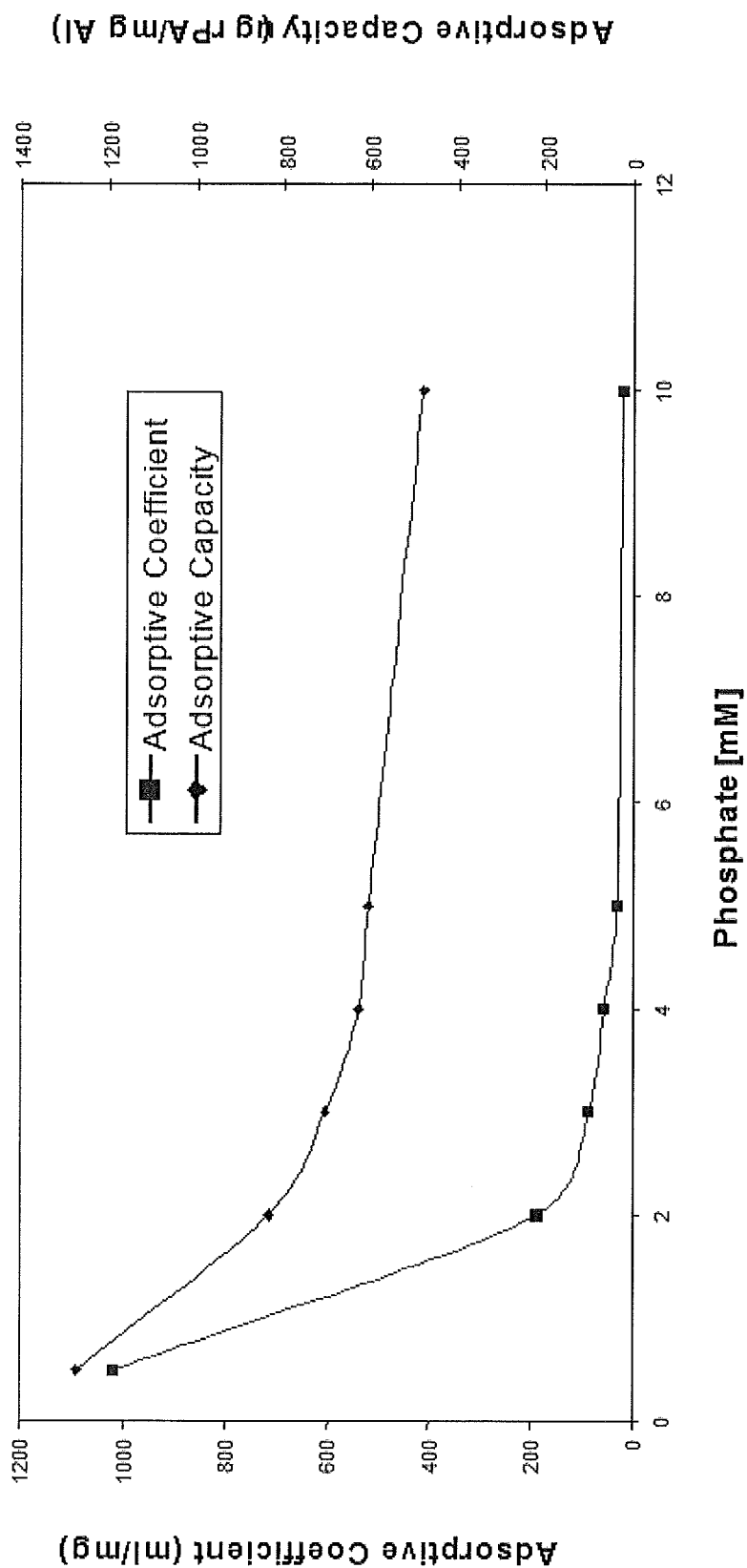
FIG. 5 shows the effect of phosphate on adsorptive capacity and adsorptive coefficient of rPA binding to alhydrogel as determined by Langmuir analysis.
Figure 7:
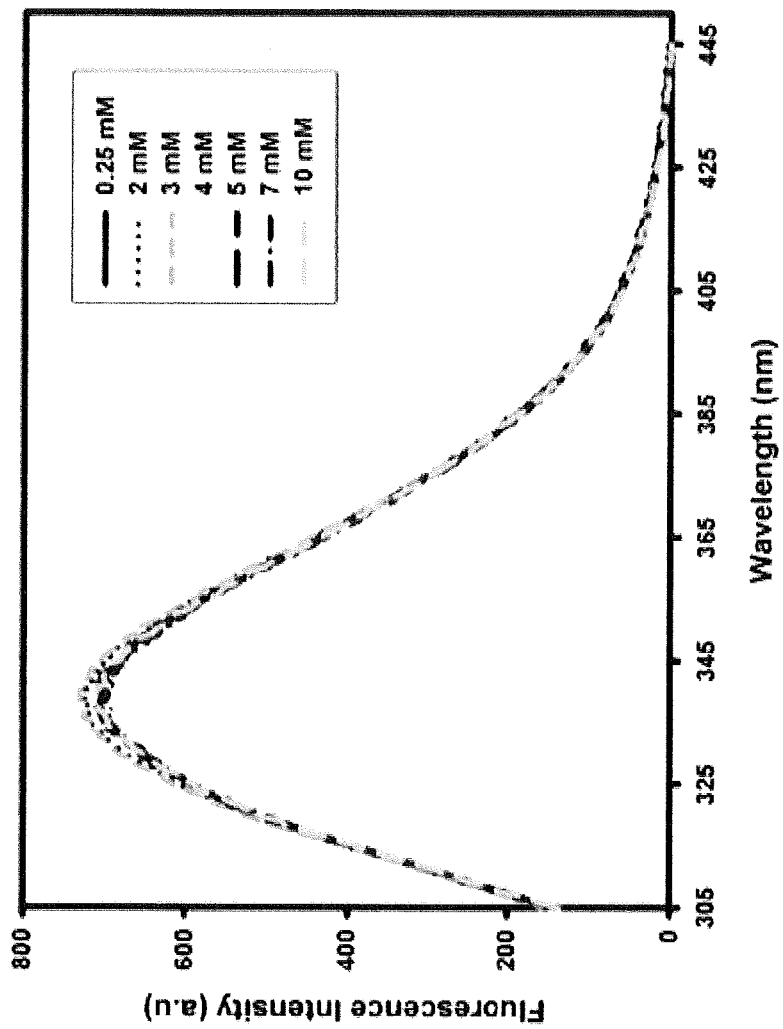

A brief description of the rPA drug product manufacturing process is presented below, along with a process diagram (FIG. 1). Drug substance is removed from −70° C. storage and allowed to thaw at 2-8° C. While the bulk drug substance solution is thawing, three different solutions are prepared and utilized in the formulation process, namely Solutions A to C. Solution A is the stock 0.5 M phosphate buffer, which is subsequently used to produce Solution C (phosphate buffered 0.9% saline, containing 0.04% Tween 20). It is Solution C that is used to dilute the rPA drug substance to the required concentration. Solution B comprises 1.22% saline, which is used to balance up the osmolality of the alhydrogel. The differences between the original low phosphate process and the modified high phosphate process is the concentration and pH of phosphate in Solution C.

Once the rPA drug substance is thawed and the rPA protein concentration determined by the A280 nm in-process assay, this material was sterile filtered along with the appropriate amounts of Solution C and Solution B, into the formulation vessel. Once mixed, sterile alhydrogel was added, with continuous mixing to produce the drug product formulation, i.e. 200 ug/ml rPA, 0.26% alhydrogel in phosphate buffered 0.9% saline. The formulation is stirred for 2 hours before being filled into syringes or other appropriate containers.

It was found that for the low phosphate formulation, the pH at release was 5.9 for the resulting materials used in the clinic. In contrast the pH of the high phosphate material was approximately 7.2 at release. Consequently it can be concluded that the increase in phosphate concentration was successful in its aim of controlling the pH at a neutral/physiological value.

A mouse challenge potency assay was used to test and release all batches of drug product. This assay demonstrated that the Drug Products were all potent when manufactured.

In order to be able to make comparative assessments of batch potency, the $ED_{50}$ value (a measure of effective dose) was derived from the assay data. Surprisingly, this showed that the high phosphate batches produced a significant enhancement in the potency when compared with the low phosphate batches. Moreover, the data from the high phosphate formulation were much more consistent than those from the low phosphate formulation (as indicated by the smaller error bars in FIG. 2). Thus, the modification to the phosphate concentration unexpectedly resulted in a marked enhancement of the drug product potency.

To determine the acceptable operating range for phosphate in the rPA drug product process/formulation a series of studies have been performed to evaluate the effect of phosphate concentration upon both the protein and the alum colloid. The results of these studies are presented below.

To evaluate the effect of phosphate on the alhydrogel particles the zeta potential of the alum colloidal particles was determined. Drug product and alum diluent were freshly formulated with a phosphate concentration range of 0.25 mM to 5 mM and the zeta potential was measured at T=day 0 and T=day 7. The results revealed that with increasing phosphate concentration the zeta potential became more negative, with the point of no charge being between 2 and 3 mM phosphate (FIG. 3). It was also evident that the zeta potential, of both the drug product and the diluent, had not reach equilibrium during formulation but continued to change over the preceding 7 days. This data indicated that the phosphate-alum interaction continued following formulation. However, by extrapolation to the zeta potential drug product batch data, which indicated that the high phosphate drug product batches had a zeta potential of approximately −20 mV (FIG. 5), the interaction may be reaching completion by day 7.

Comparison of the rPA drug product and diluent zeta potential values indicated that at low phosphate levels (0.25 mM) the bound protein modified the zeta potential of the formulation, however this effect was not evident when the zeta potential became negative with increasing phosphate.

It is well established that phosphate concentration has a marked effect upon the ability of rPA to bind to alhydrogel. Early in drug product development, the effect of phosphate on rPA-alum interaction was evaluated, however this was performed using a phosphate range of 10 to 400 mM. This experiment has been repeated, except that this time the effect of ≤10 mM was evaluated.

Increasing the concentration of phosphate inhibited rPA-alum binding (FIG. 4). At the 10 mM level, the % unbound rPA was at 12%, which was within the FDA guideline value of 30% unbound antigen.

Langmuir analysis was used to assess the effect of phosphate on rPA binding to alhydrogel. This analysis is used to determine the adsorptive coefficient (measure of binding strength) and adsorptive capacity (binding capacity) of molecules binding to particles.

As shown in FIG. 5, the adsorptive coefficient of rPA binding to alhydrogel was effected by the phosphate concentration, producing a biphasic curve. Following a steep drop in value, the adsorptive coefficient reached a plateau around 3-4 mM phosphate, which suggested that phosphate ions were capable of modulating the strength of rPA-alum binding. Certainly the effect of phosphate ions on the surface charge of the alum, making it more negative, would support this observation. The rPA protein is an acidic protein that would have a stronger interaction with the positively charged alum particles as opposed to the phosphate-modulated negatively charged particles.

What is also evident from the Langmuir analysis is that the adsorptive capacity of the alum also changed with increasing phosphate concentration. This binding capacity parameter was starting to reach a plateau around 3-4 mM. It should be noted that this adsorptive capacity was in excess of what was required to bind rPA at 200 ug/ml with a concentration of 0.26% alhydrogel.

The specialized drug product far UV circular dichroism technique was used to evaluate the effect of phosphate concentration on rPA secondary structure in drug product. rPA Drug Product was formulated with a range of phosphate concentrations (0.25 mM to 10 mM) and the dichroism spectra were determined between 190 nm and 250 nm. All the spectra (not shown) produced were characteristic of rPA with a minima at 208 nm and a plateau region around 216 nm (FIG. 6). Furthermore, all the spectra essentially overlapped, indicating that phosphate concentration was not affecting the secondary structure of the rPA protein in freshly formulated drug product.

Similarly, intrinsic fluorescence was used to evaluate the effect of phosphate concentration on rPA tertiary structure in drug product. rPA Drug Product was formulated with a range of phosphate concentrations ranging from 0.25 mM to 10 mM and the fluorescence emission spectra were determined. As shown in FIG. 7, all the spectra effectively overlapped each other, irrespective of the phosphate concentration, indicating that there was no effect upon λmax and hence protein tertiary structure Both intrinsic fluorescence and far UV circular dichroism indicated that phosphate concentration did not effect the rPA secondary/tertiary structure in freshly formulated drug substance. However, because it is known that the rPA protein physically binds to the alum particles and becomes immobilized, we determined whether there was a difference in rPA-alum binding, which did not significantly perturb rPA structure upon binding, a thermal denaturation approach was adopted. DSC analysis was used as an alternative measure of rPA-alum interaction. It was reasoned that immobilizing rPA on alum would reduce heat capacity changes associated with protein melting because of the restricted movement of the anchored protein and this would be detected by DSC.

When differential scanning calorimetry (DSC) was applied to freshly formulated drug product over a phosphate concentration range of 0.25 mM to 50 mM, no melting transition was detected with the 0.25 mM formulation. As the phosphate concentration increased to 2 mM, a transition was detected, which increased in both enthalpy and in melting temperature with increased phosphate concentration (FIG. 8).

Overall, the DSC supported the observation that increasing phosphate levels reduced the strength of binding of rPA to alum, as evident by the increased heat capacity of the protein. The data also suggests that the stability of the protein increases inversely proportional to the amount it is bound to the alum, as shown be the increasing melting temperature value. Although with the values for 10 and 50 mM phosphate the signal from unbound rPA would start to become significant and would contribute disproportionately to the isotherms.

Figure 9:
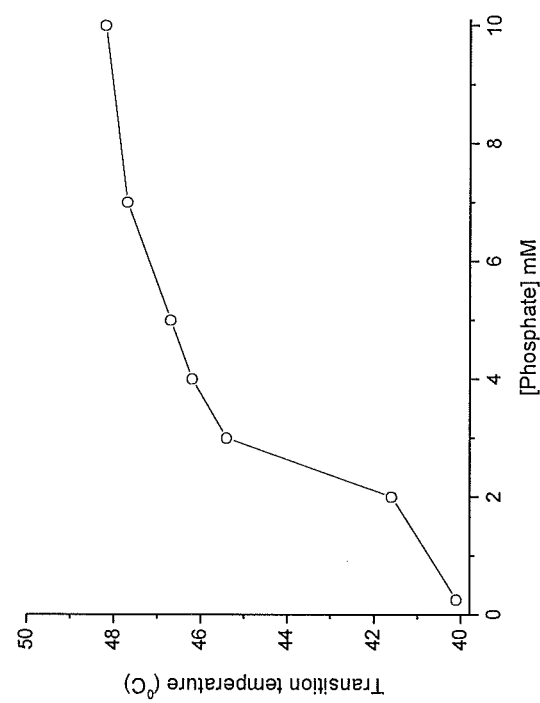

The effectiveness of the thermal denaturation approach to evaluate the rPA structure within drug product, as demonstrated in the DSC data, suggested that this could also be applied to intrinsic fluorescence. Hence, fluorescence intensity/thermal denaturation was used to determine the effect of phosphate on the melting temperatures of the protein bound to alhydrogel (FIG. 9). Similar to that shown with DSC, drug products formulated in low phosphate (0.25 mM to 2 mM) revealed little or no protein melting transition in the 40-50° C. range, whereas a transition was detected at 3-10 mM, around 46° C. When the data is plotted as melting temperature (midpoint of thermal transition) against phosphate it can be seen that the biphasic curve starts to reach a plateau at 3 mM phosphate.

In order to assess whether the increase in phosphate results in the rPA protein binding in a different manner or orientation, studies were performed using the epitope recognition assay (also known as the Drug Product immunoassay). This is effectively a protein structure assay that measures the ability of selected monoclonal antibodies to recognize specific rPA domain 4 epitopes. Domain 4 was chosen since there is evidence that this region of the protein is crucial for conferring antibody protection (Flick-Smith et al, Infect Immun., Vol. 70(3), pp. 1653-6 (2002)), A recombinant carboxy-terminal domain of the protective antigen of *Bacillus anthracis* protects mice against anthrax infection).

Two monoclonal antibodies raised against separate rPA domain 4 epitopes were used to evaluate rPA binding: (1) a stability-indicating epitope (C3 clone) and (2) a protective/stability-indicating epitope (2D4J clone). Epitope mapping of the two antibodies demonstrated that they were both binding to separate loop regions within rPA domain 4; moreover the 2D4J clone was specifically binding to the receptor binding region, which would account for its protective properties.

Figure 10:
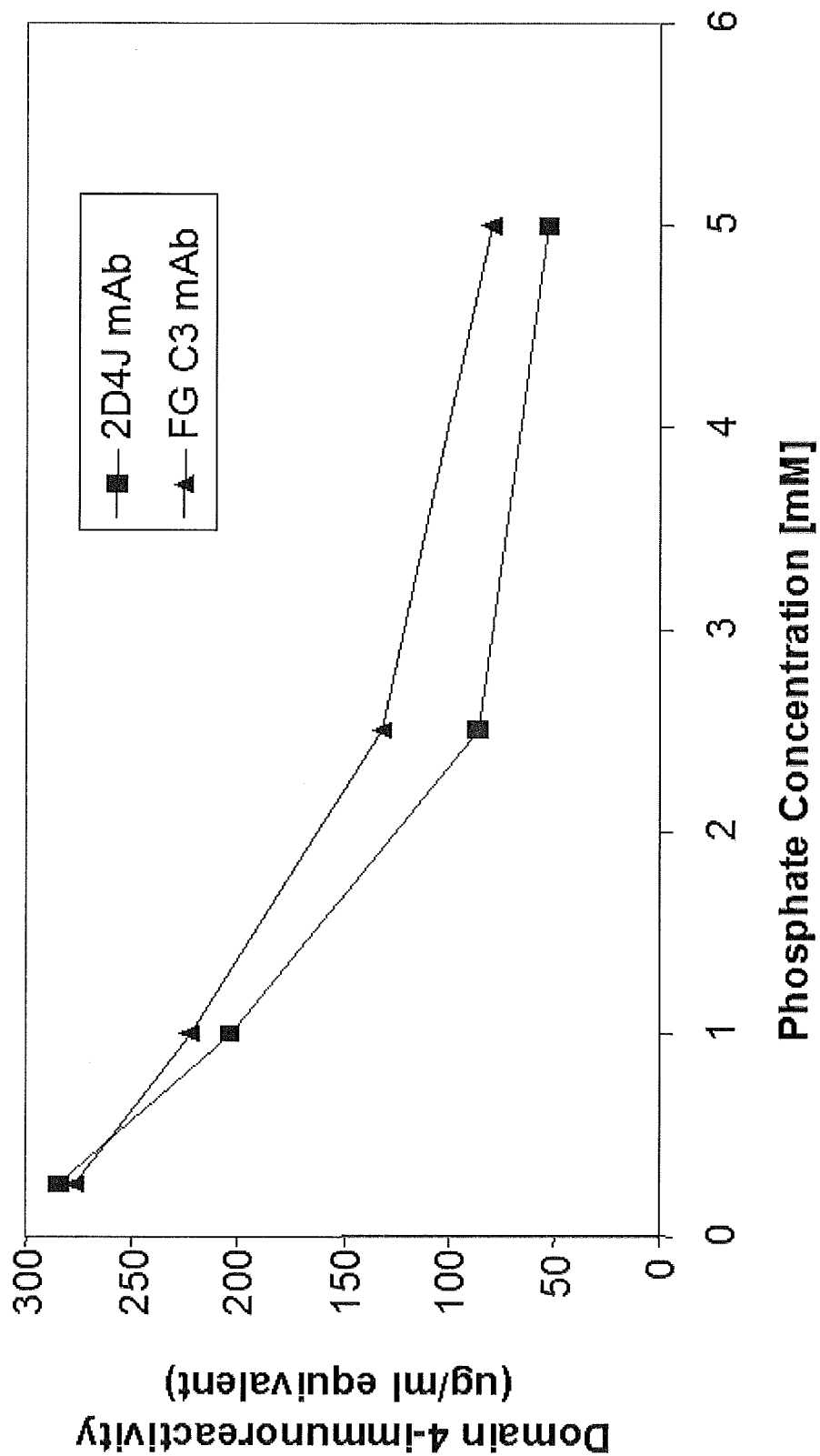

Epitope recognition analysis was performed with increasing concentrations of phosphate. With both monoclonals there was a reduction in antibody binding as a result of the increase in phosphate concentration (FIG. 10). With this assay it was not possible to evaluate a large number of phosphate concentrations due to limitations in capacity. However, from the limited number of phosphate concentrations it was seen that the immunoreactivity with both monoclonals declined rapidly up to an inflexion point around 2.5 mM, after which the rate of decline in immunoreactivity was decreased. This reduction in immunoreactivity was not due to loss of protein since all rPA effectively bound to the alum.

One unexpected conclusion of the above experiments was that phosphate must henceforth be considered as a drug product formulation critical parameter, due to its effect upon both the formulation characteristics and potency. This is particularly important since up until this point the drug production process was not designed to manufacture rPA drug product with a fixed phosphate concentration. With this old process, rPA drug substance was diluted with a phosphate buffer to reach a specific rPA protein concentration. Since the rPA concentration of the drug substance could potentially vary from the target concentration by a factor of about 17%, the amount of diluting phosphate buffer changed depending on the starting concentration of the drug substance. Since it was the volume of this phosphate that dictated the overall phosphate concentration, the levels of this inorganic ion would vary appropriately. Subsequent modifications to the drug product process have been made to ensure that a constant phosphate concentration was formulated, irrespective of the drug substance concentration at the start of the process.

What is claimed is:

1. An anthrax vaccine, consisting of a therapeutically effective amount of recombinant anthrax protective antigen (rPA) bound to aluminum hydroxide, and a phosphate salt at a concentration in the range of 2.5 to 4.5 mM.

2. The anthrax vaccine of claim 1, wherein said phosphate salt concentration is about 4 mM.

3. The anthrax vaccine of claim 1, wherein said rPA is present at about 100 to 300 µg/ml.

4. The anthrax vaccine of claim 1, wherein said rPA is present at 150 to 250 µg/ml.

5. The anthrax vaccine of claim 1, wherein said rPA is present at 10 to 300 µg/ml.

6. The anthrax vaccine of claim 1, wherein the pH of said vaccine is in the range of 7.0 to 7.2.

7. The anthrax vaccine of claim 1, wherein said rPA is presented at about 100 µg/ml, said phosphate is present at about 4.0 mM, said aluminum hydroxide is present at about 0.26% by weight and wherein the pH of said vaccine is about 7.1.

8. The anthrax vaccine of claim 1, wherein said rPA is present at about 50 to 300 µg/ml.

9. The anthrax vaccine of claim 1, wherein said phosphate salt concentration is present in the range of 3.8 mM to 4.2 mM.

10. The anthrax vaccine of claim 1, wherein said phosphate salt concentration is present in the range of 3.9 mM to 4.1 mM.

11. The anthrax vaccine of claim 1, wherein said phosphate salt concentration is present in the range of 3.5 mM to 4.5 mM.

12. A method of protecting against a disease caused by an anthrax infection comprising administering to a mammal at risk of such an infection a therapeutically effective amount of the vaccine composition of claim 1.

13. The method of claim 12, wherein said mammal is a human being.

14. A method of protecting against a disease caused by an anthrax infection comprising administering to a mammal at risk of such an infection a therapeutically effective amount of the vaccine composition of claim 7.

15. A method of treating a bacterial infection in a mammal, comprising administering to a mammal afflicted with such infection a therapeutically effective amount of the vaccine composition of claim 1.

* * * * *